(12) United States Patent
Sugimoto

(10) Patent No.: US 9,480,542 B2
(45) Date of Patent: Nov. 1, 2016

(54) JIG FOR BITE ALIGNMENT IN DENTISTRY AND BITE REGISTRATION METHOD USING THE SAME

(76) Inventor: Yuji Sugimoto, Ishikawa (JP)

(*) Notice: Subject to any disclaimer, the term of this patent is extended or adjusted under 35 U.S.C. 154(b) by 6 days.

(21) Appl. No.: 13/981,831

(22) PCT Filed: Dec. 9, 2011

(86) PCT No.: PCT/JP2011/078526
§ 371 (c)(1),
(2), (4) Date: Jul. 29, 2013

(87) PCT Pub. No.: WO2012/101914
PCT Pub. Date: Aug. 2, 2012

(65) Prior Publication Data
US 2013/0309631 A1    Nov. 21, 2013

(30) Foreign Application Priority Data
Jan. 28, 2011    (JP) .................. 2011-017029

(51) Int. Cl.
*A61B 9/00*    (2006.01)
*A61C 8/00*    (2006.01)
(Continued)

(52) U.S. Cl.
CPC ............. *A61C 8/0001* (2013.01); *A61C 11/06* (2013.01); *A61C 19/05* (2013.01)

(58) Field of Classification Search
CPC ...... A61C 5/125; A61C 8/0001; A61C 9/00; A61C 9/0006; A61C 9/0013; A61C 19/04; A61C 19/05; A61C 19/066; A61C 8/005; A61C 8/006; A61C 8/0048; A61C 8/0054; A61C 8/0068

USPC ............. 433/37–47, 68, 70, 71, 74, 214
See application file for complete search history.

(56) References Cited

U.S. PATENT DOCUMENTS

| 2,171,759 A | * | 9/1939 | Meyer ..................... 433/213 |
| 5,401,170 A | | 3/1995 | Nonomura |
| 5,597,303 A | * | 1/1997 | Simmons ............... A61C 19/05 |
| | | | 433/69 |

(Continued)

FOREIGN PATENT DOCUMENTS

| JP | S60-99915 U | 7/1985 |
| JP | H05-184601 A | 7/1993 |

(Continued)

OTHER PUBLICATIONS

Oxforddictionaries.com. Definition of integral [retrieved on Oct. 19, 2014]. Retrieved from the Internet: http://www.oxforddictionaries.com/us/definition/american_english/integral.*

*Primary Examiner* — Nicholas Lucchesi
*Assistant Examiner* — Matthew Saunders
(74) *Attorney, Agent, or Firm* — Manabu Kanesaka

(57) ABSTRACT

A jig for bite alignment in dentistry enables to achieve precise bite registration without using the wax rim, and a bite registration method and a manufacture method of dentures using the jig for bite alignment. Using the jig for bite alignment in dentistry provided with the bite material fixing portion in which the bite material is arranged for recording the occlusal position of teeth and with the implant connecting portion for attaching and detaching the implant arranged in oral cavity, the implant connecting portion is mounted on the implant buried in the alveolar bones of an oral cavity to record the occlusal position of teeth through the bite material arranged in the bite material fixing portion.

8 Claims, 10 Drawing Sheets

(51) Int. Cl.
*A61C 11/06* (2006.01)
*A61C 19/05* (2006.01)

(56) References Cited

U.S. PATENT DOCUMENTS

| | | | |
|---|---|---|---|
| 5,947,736 A * | 9/1999 | Behrend | 433/214 |
| 6,213,773 B1 * | 4/2001 | Gittleman | 433/172 |
| 6,382,977 B1 * | 5/2002 | Kumar | 433/214 |
| 6,666,684 B1 * | 12/2003 | Names | 433/173 |
| 2003/0044749 A1 * | 3/2003 | Marotta | 433/45 |
| 2007/0196782 A1 | 8/2007 | Noguchi | |
| 2007/0281278 A1 * | 12/2007 | Jorneus et al. | 433/173 |
| 2009/0220916 A1 | 9/2009 | Fisker et al. | |
| 2010/0196855 A1 * | 8/2010 | Muller | A61C 8/0001 433/193 |
| 2010/0248180 A1 * | 9/2010 | Bondar | 433/141 |
| 2012/0052463 A1 * | 3/2012 | Pollet | 433/172 |
| 2012/0088208 A1 * | 4/2012 | Schulter et al. | 433/173 |
| 2013/0157217 A1 * | 6/2013 | LeBeau | 433/68 |

FOREIGN PATENT DOCUMENTS

| | | |
|---|---|---|
| JP | 2005-152106 A | 6/2005 |
| JP | 3771534 B | 2/2006 |

* cited by examiner

JIG FOR BITE ALIGNMENT IN DENTISTRY AND BITE REGISTRATION METHOD USING THE SAME

RELATED APPLICATIONS

The present application is National Phase of International Application No. PCT/JP2011/078526 filed Dec. 9, 2011, and claims priority from Japanese Application No. 2011-017029, filed Jan. 28, 2011.

The present invention relates to a jig for bite alignment in dentistry used for making and adjusting dentures such as crowns, bridges, and complete dentures and for inspecting the oral cavity, and also relates to a bite registration method using the same.

BACKGROUND OF THE INVENTION

In the past, in making dentures such as crowns, bridges, and complete dentures, at first an impression of oral cavity is taken (impression taking) and next a work called as bite registration, that is, a work of recording the positional relationship between the maxillary teeth and the mandibular teeth by means of the wax rim. This work is called "Bite Taking (BT)" in health insurance terms. By recording the occlusal position of teeth via this bite registration, a working model can be mounted on an articulator in the conditions similar to the actual shape of oral cavity, and then, on the working model, inspection can be made or the prosthesis can be made and adjusted. An articulator is a device which can simulate the jaw movement and the various occlusal positions on a working model for treatment and research in dental care. As articulators, various forms of apparatuses are developed according to the purpose such that the specific occlusal position such as centric occlusion is reproduced or the jaw movement such as lateral movement and protrusive sliding movement is reproduced (Patent Document 1).

A process of making artificial teeth involves that at first a primary impression is taken using impression materials and a gypsum model obtained from the primary impression is used to make the "tray" for taking impression, which is called the individual tray and then used to take precise impressions. The tray is actually put into the mouth to take impressions by making various movements such as chewing, pursing the lips, and protruding the tongue. Then, an impression material with high reproduction performance is then poured into the tray to obtain the precise impression. Impressions thus obtained are used to fabricate a gypsum model, which is the base (working model) for the dental technician to make dentures with technical operations.

Most important thing in fabrication of artificial teeth (denture) is "occlusion". While the vertical dimension (also called occlusal vertical dimension, rest position, and high-low dimensions) is generally considered to be important for occlusion, alignment of the maxillary teeth and the mandibular teeth is not so simple but many measurements such as determination of the positions of the dental midline, the anterior teeth, and the horizontal jaw in addition to the position of the maxilla and mandible have to be performed. Furthermore, the measurements are not useful until they are performed under the conditions in which the bite registration is achieved on the firmly secured base.

Patent Document 1 discloses an occlusion adjustment apparatus in making dentures and Patent Document 2 discloses a method of recording information about the mandible using the recording bases for fabrication of dentures.

PATENT DOCUMENTS

Patent Document 1: Japanese Patent Publication No. 3771534.
Patent Document: Japanese Patent Application Laid-Open (JP-A) 2005-152106.

BRIEF SUMMARY OF THE INVENTION

In a work called as bite registration, the positional relationship of teeth is recorded on a wax rim, which is an artificial rim made of wax (it may take U-shape in case of complete dentures while it may take the shape corresponding to the damaged portion in case of partial dentures). In making of the wax rim, the real model is filled with a resin to mold just like molding an individual tray, followed by glazing a wax. And then, the wax rim is put into the patient's mouth for determining the occlusal position. In FIG. 15, the denture S is placed on the articulator K and the wax rim T lies between them. This arrangement is held in the actual oral cavity. FIG. 14 is a flowchart for making dentures starting from bite registration. The wax rim is supposed to be used in Patent Documents 1 and 2.

However, there is a problem in which the bite registration with the wax rim T cannot provide precise occlusion of the maxillary and mandibular teeth. According to the findings of the present inventors, its cause may be, in addition to known factors such as occlusal timing, deformation of the base of the oral cavity (gingival portion). Especially, if the gingival portion is deteriorated just as with the elderly, it is difficult to record the precise occlusal position by putting a wax rim into the oral cavity.

Also, the present inventors presume that for example, when there is not a full set of teeth and even one tooth is missed, occlusion cannot occur at such a position, but in the reference position of occlusion such as back teeth, precise occlusion can be obtained if occlusion can occur at such a position.

On the other hand, for dental technicians, often not dental technicians but dentists actually confirm the occlusal condition (there is little dental clinic with a dental technician). Therefore, while dental technicians make dentures such as crowns, bridges, and complete dentures with precisely reproducing the wax rim, some discrepancy with the images of dental technicians may occur when a patient wears the dentures at dental clinic.

In the conventional bite registration using the wax rim, there is a large burden for patients since large amounts of the base plate wax is put into the mouth while keeping the mouth widely open. In addition, there are also the above-described problems. The present inventors presume that if precise bite registration can be achieved without using the wax rim, a waste due to material cost can be eliminated and the operation process can be shortened.

Thus, the purpose of the present invention is to provide a jig for bite alignment in dentistry enabling to achieve precise bite registration without using the wax rim, and a bite registration method using the jig for bite alignment.

A jig for bite alignment in dentistry of the present invention is provided with a bite material fixing portion in which a bite material for recording the occlusal position of teeth is arranged and an implant connecting portion for attaching and detaching an implant arranged in oral cavity, and is characterized in that the implant connecting portion is mounted on the implant to record the occlusal position of teeth through the bite material arranged in the bite material fixing portion.

Also, a bite registration method of the present invention uses a jig for bite alignment in dentistry provided with a bite material fixing portion in which a bite material for recording the occlusal position of teeth is arranged and an implant connecting portion for attaching and detaching an implant arranged in oral cavity, and is characterized in that the implant connecting portion is mounted on the implant in oral cavity to record the occlusal position of teeth through the bite material arranged in the bite material fixing portion.

According to the present invention, the implant connecting portion of a jig for bite alignment in dentistry is mounted on an implant arranged in oral cavity to record the occlusal position of teeth with a bite material arranged in a bite material fixing portion so that precise bite registration can be achieved through occlusion of teeth based on the implant firmly secured to the alveolar bones. And, after recording the occlusal position of teeth with the bite material arranged in the bite material fixing portion, the jig for bite alignment in dentistry used for the recording of the bite alignment (bite registration) is taken out to mount on a working model for reproducing the occlusion of teeth similar to the actual state in oral cavity, and then, on the working model, inspection can be made or the prosthesis can be made and adjusted. Since the jig is small and a small amount of the bite material is used, a burden to patients is small as compared to a wax rim in which large amounts of material is used while keeping mouth widely open.

According to the present invention, the jig for bite alignment in dentistry and the implant preferably have a concave portion and a convex portion fitting with the concave portion, and the cross-sections of the concave and the convex portions are formed in the shape of polygon and the mounting angle can preferably be varied in the circumferential direction.

According to the present invention, for example, the implant connecting portion having a convex portion with a shape corresponding to the concave portion of the buried implant is fitted to the concave portion with a shape of triangle, hexagon or the like to record the fitting position (e.g. by marking) so that a working model for reproduction can be attached to the working model for reproduction by means of the record (e.g. marking) after taking out the jig for bite alignment used for the bite registration.

In the jig for bite alignment in dentistry of the present invention, the bite material fixing portion is preferably arranged offset from the central axis of the implant connecting portion. A bite registration method of the present invention is characterized in that the occlusal position offset from the central axis of the implant connecting portion is recorded, or while the bite material fixing portion is arranged offset from the central axis of the implant connecting portion, the mounting angle of the implant connecting portion can be varied with respect to the implant to record the occlusal position at several positions.

According to the present invention, for example, in the position where teeth are missed, in case of which implants are apart from the opposing teeth, and in case of which the position of alveolar crest (alveolar ridge and alveolar process) is offset and different from the position of the implant, alignment of the bite material fixing portion allows for recording of the occlusal position even in the position where teeth are missed. Also, when alignment of the bite material fixing portion with respect to the hypothetical occlusal position allows for recording of the occlusal position even in such a position.

According to the bite registration method of the present invention, the occlusal position is recorded at several positions by rotating the implant connecting portion with respect to the implant. Therefore, even if the occlusal timing in one of the recordings is not appropriate, the consistency between the one recording and the other recordings can be studied.

The bite registration method of the present invention is characterized in that, in order to make dentures for teeth adjacent to each other such as complete dentures and bridges, the jigs for bite alignment in dentistry are arranged on plural locations in oral cavity to record plural occlusal positions.

According to the present invention, for example, complete dentures can be constructed by recording (height position and angle) the occlusion at plural locations such as three locations of the right and left back teeth and the front tooth, and in case of bridges, precise bite registration can be achieved by measurements at plural locations by placing the jig for bite alignment in dentistry at two positions of both ends.

In the manufacture method of dentures of the present invention, it is preferred that the jig for bite alignment after the recording with the bite registration material is taken out of oral cavity and mounted on a working model for reproducing the occlusion of teeth similar to the actual state in oral cavity, and then, on the working model, the dentures such as crowns, bridges, and complete dentures. The dentures include prostheses such as crowns and metal frames.

According to the present invention, the jig for bite alignment in dentistry is used while placing on a stable base. Therefore, precise occlusion can be reproduced on an articulator, enabling to make dentures corresponding to the state of patient's oral cavity without using a wax rim.

According to the present invention, the implant connecting portion is mounted on an implant arranged in oral cavity to record the occlusal position of teeth with a bite material arranged in the bite material fixing portion so that bite registration can be performed with firmly securing the jig to the alveolar bones. And, after the occlusal position of teeth is recorded with a bite material arranged in a bite material fixing portion, the jig for bite alignment in dentistry is taken out to mount on a working model for reproducing the occlusion of teeth similar to the actual state in oral cavity, and then, inspection can be made or the prosthesis can be made and adjusted. Therefore, a wax rim used in conventional bite registration is not required resulting in substantial saving of expense. Also, since the jig for bite alignment used is much smaller than a conventional wax rim, a burden to patients can be reduced and storage and maintenance can be made easier, particularly for dental technicians. Also, in the past it has to spend several days to take impressions and fabricate the maxillary and mandibular models which are used to make a wax rim. However, according to the bite registration of the invention in the present application, if the occlusal position is recorded once with a jig for bite alignment in dentistry of the present invention, occlusion can be reproduced by mounting the maxillary and mandibular models on an articulator at the same time as or even prior to bite registration so that the number of manufacture processes can be reduced, the period for making dentures can be shortened, and the frequency of patient's examination can be reduced. Also, since the jig for bite alignment in dentistry of the present invention is small in size, a burden to patients can be reduced. And since only an amount of a bite material is used to arrange it in a bite material fixing portion, the amount thereof can be reduced.

Further, according to the present invention, the occlusal position of teeth even in the position in which patient's teeth are missed can be recorded using an eccentric bite material fixing portion. And, in making dentures for teeth adjacent to each other such as complete dentures and bridges, dentures can be made with good precision by arranging the jig for bite alignment at plural positions in oral cavity.

DETAILED DESCRIPTION OF THE INVENTION

Hereinafter, a specific embodiment to which the present invention is applied will be described in detail with reference to drawings.

Jig for Bite Alignment in Dentistry

Figure 1:
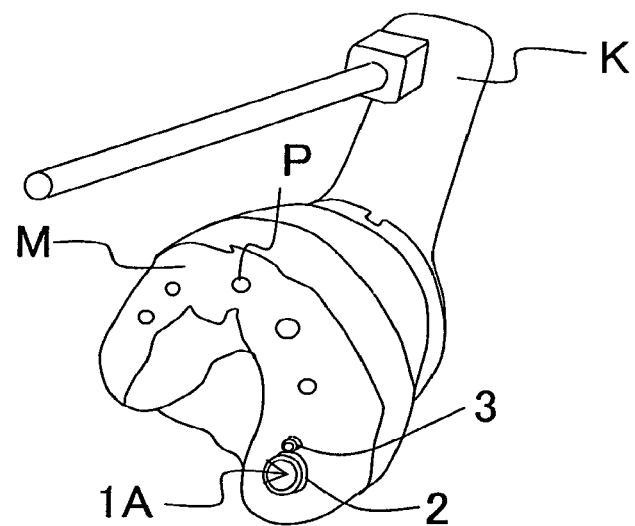
FIG. 1 is a perspective view of a jig for bite alignment in dentistry in one embodiment of the present invention, mounted on a working model attached to an articulator.
Figure 2:
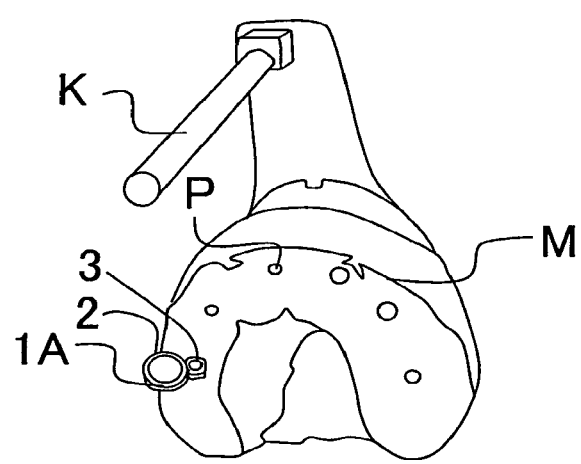
FIG. 2 is a perspective view of a jig for bite alignment in dentistry in the embodiment of the present invention, mounted on a working model attached to an articulator.
Figure 3:
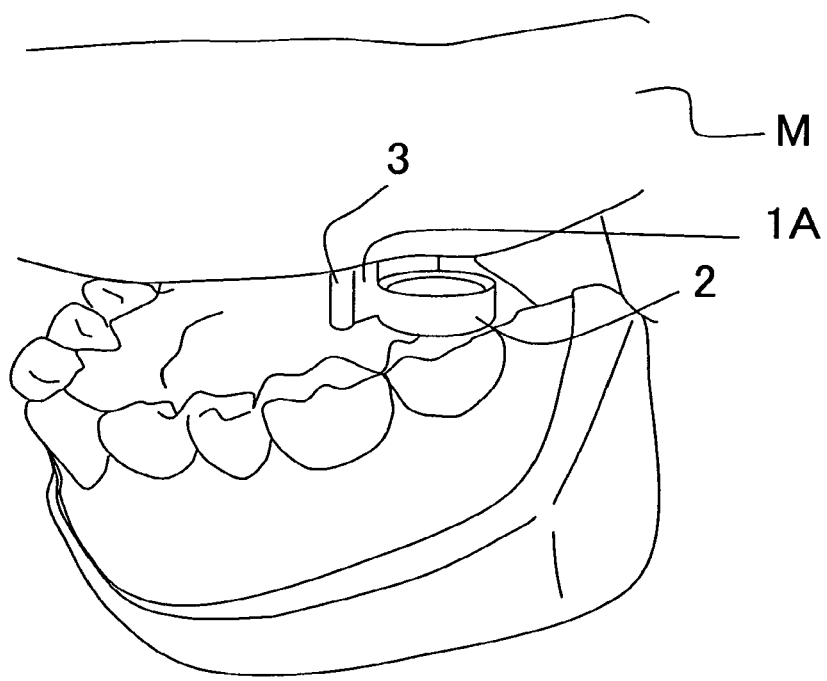
FIG. 3 is a perspective view of a jig for bite alignment in dentistry in the embodiment of the present invention, mounted on a working model attached to an articulator.
Figure 4A:
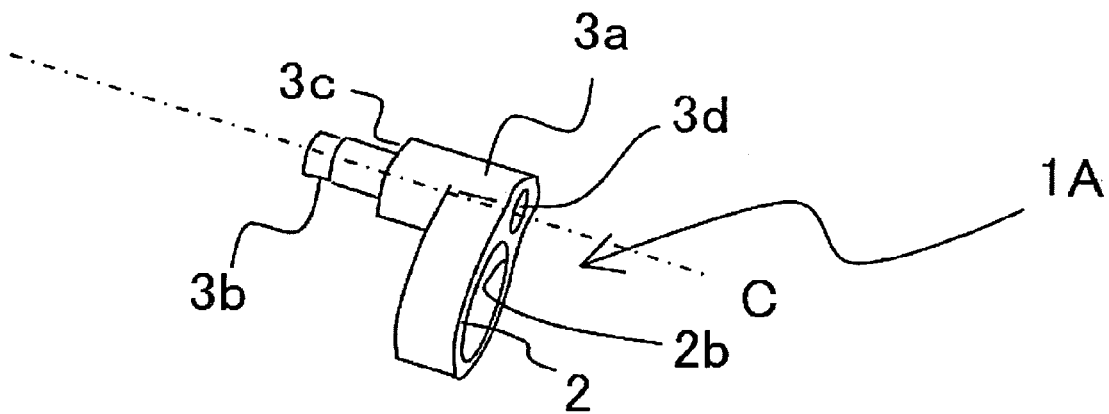
FIG. 4A is a perspective view of the jig for bite alignment in dentistry in the embodiment.
Figure 4B:
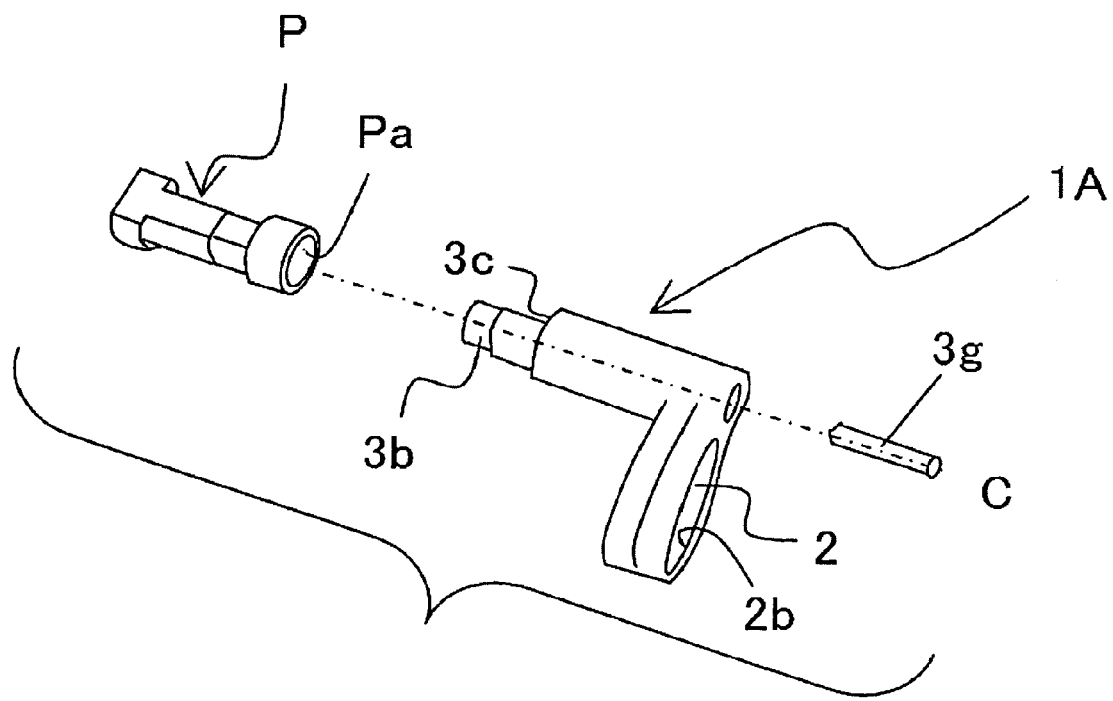
FIG. 4B is a perspective view of the jig for bite alignment in dentistry of the embodiment and an implant.
Figure 5:
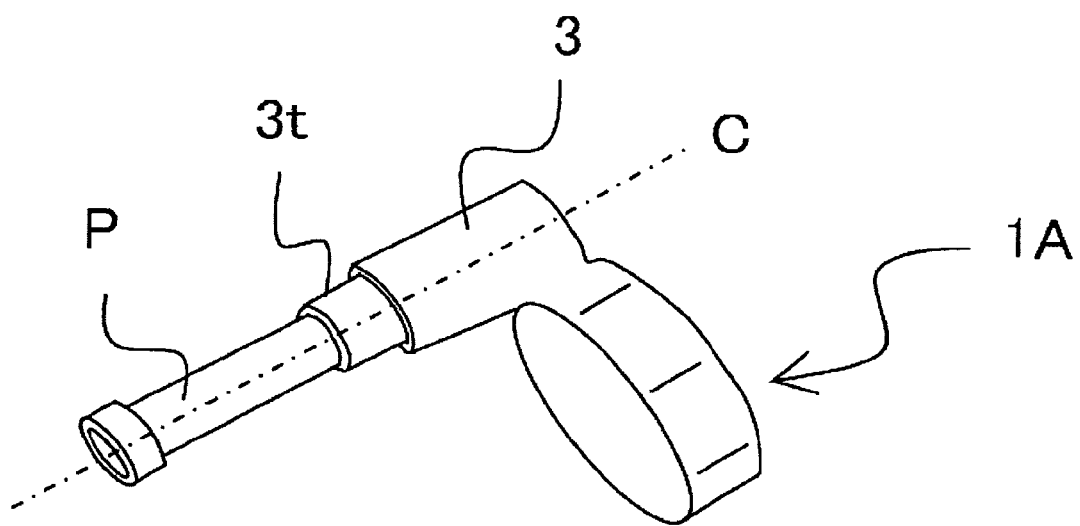
FIG. 5 is a perspective view of the jig for bite alignment in dentistry of the embodiment connected to the implant.

FIGS. 1 to 3 are perspective views of a jig for bite alignment in dentistry in the present embodiment, mounted on a working model (maxillary model). FIGS. 4A, 4B and 5 are perspective views of the jig for bite alignment in dentistry and an implant. The jig 1A for bite alignment in dentistry in the present embodiment is provided with the bite material fixing portion 2 in which the bite material 2b for recording the bite alignment is arranged and with the implant connecting portion 3 for attaching and detaching the implant P in oral cavity, and the bite material fixing portion 2 is arranged on an upper part of the implant connecting portion 3.

The implant connecting portion 3 is used for attaching and detaching an implant arranged in oral cavity. A convex large-diameter portion 3a and a small-diameter portion 3b are respectively formed in the upper and lower side of the portion 3, at the boundary of which the step portion 3c as well as three pieces of the protrusion 3t are formed. Portions corresponding to the shape of 3a, 3b, 3c, and 3t are formed in the concave portion Pa of the implant P, and three pieces of the protrusion 3t are formed with separation of 120 degrees and constituted such that the angle of the implant connecting portion 3 can be varied in the circumferential direction. That is, cross-section of the outer circumference of the small-diameter portion 3b in the implant connecting portion 3 is formed in a triangular shape (or some polygonal shapes) and the polygonal concave portion Pa corresponding thereto is formed in the implant P.

In the small-diameter portion 3b of the implant connecting portion 3, protrusions can be arranged at a specific interval on the circumference of the concave portion Pa of the implant P so as to insert into the concave portion Pa of the implant P described below for rotation and angle adjustment. Alternatively, a concave portion may be formed on the implant connecting portion 3, whereas a convex portion may be formed on the implant P. Also, as illustrated in FIGS. 4A and 4B, the jig 1A for bite alignment in dentistry comprising the implant connecting portion 3 with different length may be made and used depending on patients. On a type of the implant P, screw-type connection may be used as the implant connecting portion 3 for connecting the implant P. The shape of the circumference of the implant connecting portion 3 may be circular, the shape of the corresponding concave portion Pa of the implant P may also be circular, and one may be circular and the other may be polygonal.

Figure 11:
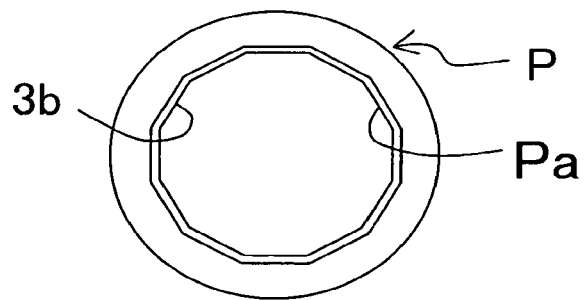
FIG. 11 is a plan view of another implant of the embodiment.

Herein, since some commercially available implants P have a concave portion whose circumferential groove has the triangular cross-section, the angle can be varied in commercially available products. However, a polygonal (dodecagonal) concave portion is preferably formed so as to allow for designing a further detail of the rotation angle (FIG. 11).

Also, the support hole 3d is formed at the center of the implant connecting portion 3 to connect and secure the implant connecting portion 3 to the implant P through the connecting member 3g (a connection screw having a screw head (FIG. 4B)).

The bite material fixing portion 2 is the area in which the bite material 2b (silicon, resins and the like) is arranged, and provided with a head portion comprising the circular concave portion 2a. A engaging hole 2c is formed at a specific position of the concave portion 2a (FIG. 6B). The engaging hole 2c is arranged so that, when a liquid form of silicon, resins and the like is poured into the concave portion 2a, it flows into the engaging hole 2c and then hardens to prevent the movement of the bite material 2b during recording the positional relationship between the maxillary teeth and the mandibular teeth through occlusion. The bite material 2b may be formed in plural layers in the vertical direction, and its height may be adjusted with a sheet-like member capable of lying at the bottom of the concave portion 2a. In the present embodiment, a size of the concave portion 2a of the bite material fixing portion 2 is slightly smaller (i.e. has slightly smaller diameter) than the teeth at which the implant P is arranged (hypothetical teeth).

In the jig 1A for bite alignment in dentistry in the present embodiment, the bite material fixing portion 2 is arranged offset from the central axis C of the implant connecting portion 3. That is, the support hole 3d is formed at the upper tip portion of the central axis C of the implant connecting portion 3 to indicate its position, from which the bite material fixing portion 2 is arranged eccentric to one side of the outer circumference. This allows for recording of occlusion at the position in which teeth are missed, for example, even when a full set of teeth is not available and some are missed. That is, occlusion at the position in which teeth (herein second molars) are missed can be recorded by inserting and securing the implant connecting portion 3 in the jig 1A for bite alignment in dentistry into the implant P, followed by disposing the eccentric bite material fixing portion 2 at the adjacent position of missed teeth. Also, the bite material fixing portion 2 can be disposed in eccentric manner at a position in the back of the implant P (a position distant from the position of the implant P) using the jig 1A for bite alignment in dentistry comprising the bite material fixing portion 2 in the eccentric position, thereby enabling to record occlusion at back of oral cavity and at the position at which no teeth is present (provided that teeth in the opposing jaw is present).

Bite Registration Method and Manufacture Method of Dentures

Next, a bite registration method and a manufacture method of dentures using the jig for bite alignment in dentistry will be described.

Figure 14:
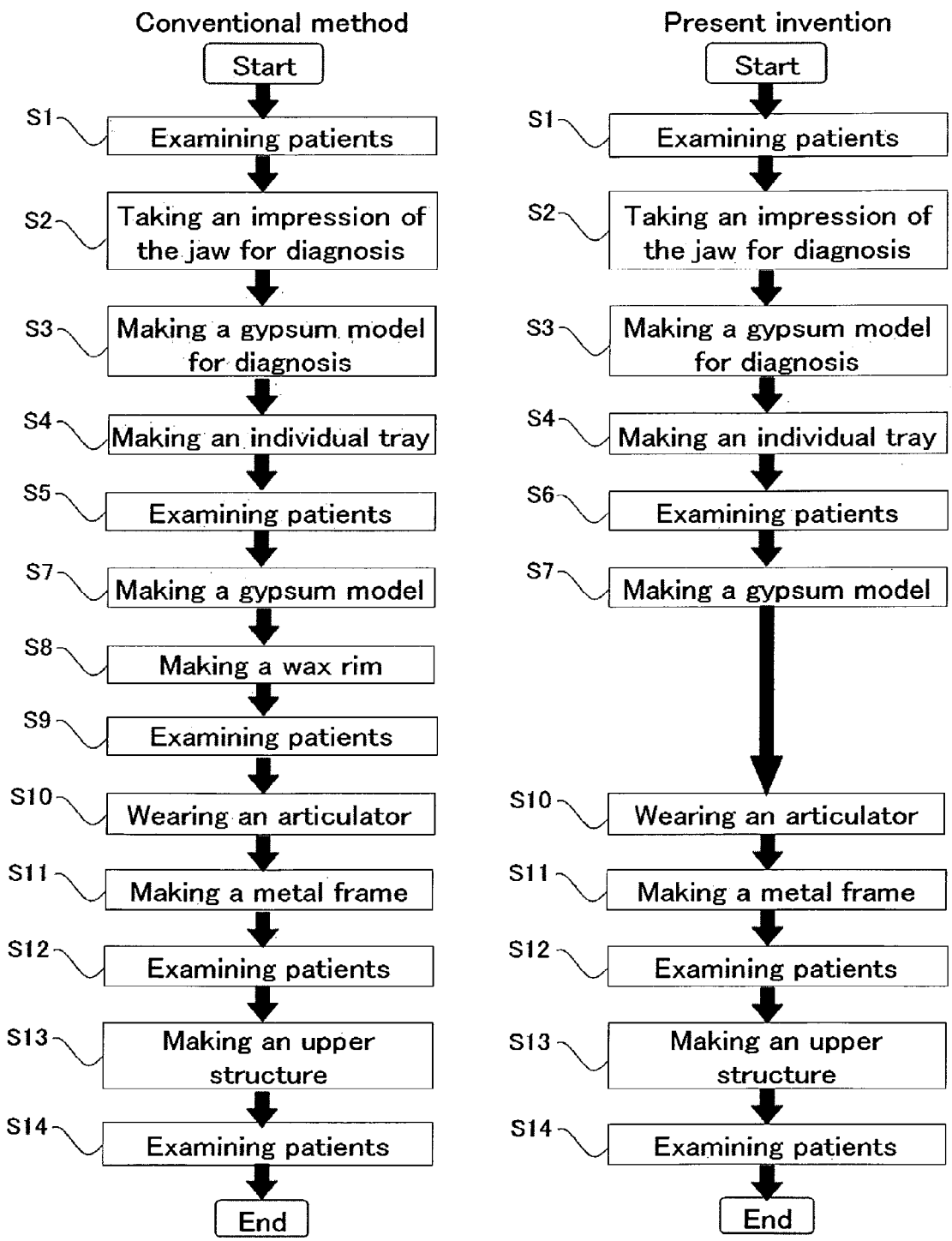
FIG. 14 is a flowchart of manufacturing a denture with a bite registration method according to one embodiment of the present invention.
Figure 15:
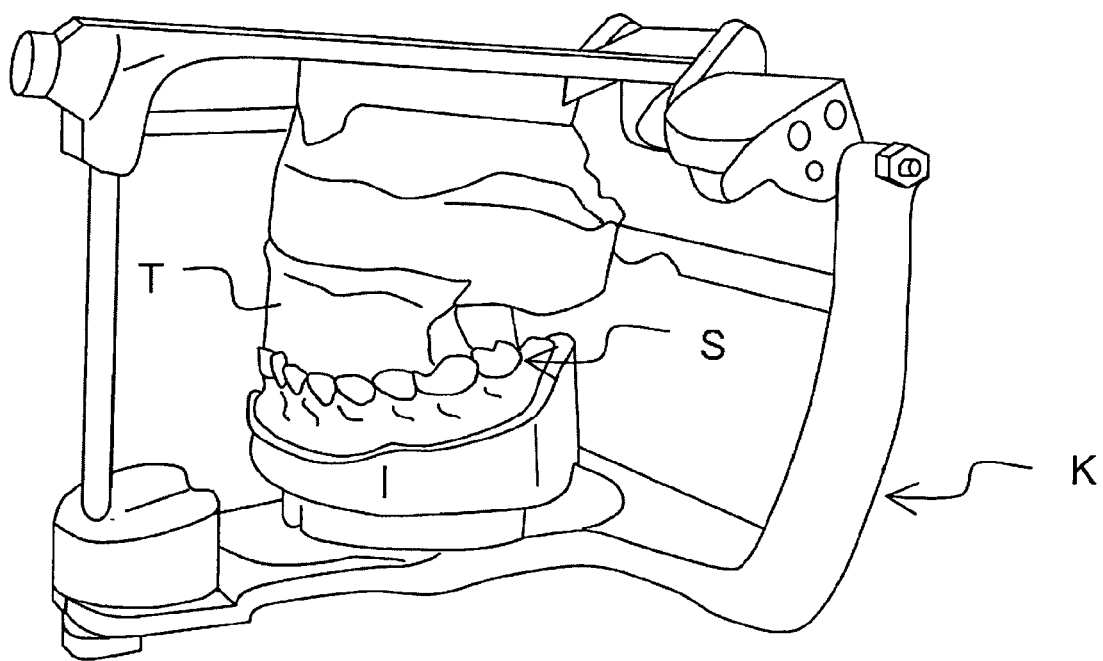
FIG. 15 is a perspective view of a conventional wax rim and the state in which the wax rim is mounted on an articulator.

The case will be described in which a maxillary complete denture is made with a metal frame denture using the jig 1A for bite alignment in dentistry comprising the bite material fixing portion 2 arranged in the eccentric position. FIGS. 1 to 3 illustrate the jig 1A for bite alignment in dentistry in the present embodiment mounted on the maxillary model M, and this state is held in the case in which the jig 1A for bite alignment in dentistry is mounted in actual oral cavity of patients. FIG. 14 is a flowchart of manufacture of dentures in the present embodiment as compared to conventional examples.

At first, after examining patients (S1) and reviewing required for the implant treatment, whether or not the implant can be performed is judged, and when possible, surgery is performed for burying a portion (fixture) of the implant P in the maxilla (alveolar bone) corresponding to the root of tooth (fixture burying surgery) (S2). It is herein presumed to bury the implants P with a specific interval over a whole area of the maxilla. Then, a gypsum model for diagnosis (S3), followed by an individual tray (S4), is made.

The jig 1A for bite alignment in dentistry is then mounted on the implant P buried in oral cavity. That is, the implant connecting portion 3 in the jig 1A for bite alignment in dentistry is mounted while adjusting the angle to fit. In this case, if the position specific for inserting the small-diameter portion 3b of the implant connecting portion 3 into the implant P is marked, it is possible to mount the jig 1A for bite alignment in dentistry on the working model M with reproducing its mounting angle by taking it out to mount on the working model M via the mark for reproducing the occlusion similar to the actual oral cavity. By means of the mark, it is possible to mount the jig 1A without examining the direction and the mounting angle.

On the other hand, while patients are examined and impression taking (precise impression using the individual tray) is performed to achieve bite registration as in the conventional methods (S5), bite registration of the present embodiment allows bite registration at the same time as or prior to impression taking by using the jig 1A for bite alignment in dentistry (S6).

In the present embodiment, the jig 1A for bite alignment in dentistry is mounted on the buried implant P at three positions of the right and left back teeth and the front tooth for making a complete denture. The jig 1A is mounted in advance on the buried implant P in oral cavity (tentative mounting) in order to determine the approximate height and horizontal position of occlusion, that is, to confirm the thickness of the bite material 2b and feel of wearing. Bite registration may be recorded by using the jig 1A for bite alignment in dentistry with the bite material 2b filled thicker in the bite material fixing portion 2.

The height of the jig 1A for bite alignment in dentistry (particularly the height of the bite material fixing portion 2) becomes an issue, provided herein that the jig is tentatively mounted in order to, for example, investigate the thickness of the bite material, but when there is an issue from the anatomic point of view or when there remains even one natural tooth, the height of the bite material fixing portion 2 is adjusted to lower than the height of the tooth to fill the concave portion 2a of the bite material fixing portion 2 with a bite material with sufficient thickness. Also, in bridges and positions with free ends the jig 1A for bite alignment in dentistry in which the height of the bite material fixing portion 2 is lower than the height of adjacent teeth (remaining teeth) is used. As illustrated in FIGS. 4A and 4B, preparation of the jig 1A for bite alignment in dentistry with various heights allows for adjusting various heights.

Next, after the jig is once taken out and the bite material fixing portion 2 is filled with the bite material 2b, it is remounted in oral cavity of patients. In the present embodiment, when the jig 1A is mounted at three positions for the right and left back teeth and the front tooth, the tip portion of the implant P abuts against the step portion 3c of the implant connecting portion 3 to determine the height. Patients are then asked to clench the teeth (see FIG. 3, bite registration in FIG. 14). Then, an impression of the patient is taken and a gypsum model is made (S7). While FIG. 3 illustrates the jig 1A for bite alignment in dentistry mounted on the maxillary model M, this state is held in the case the jig 1A for bite alignment in dentistry is mounted in actual oral cavity of patients so that a view of the jig 1A for bite alignment in dentistry mounted in actual oral cavity of patients is omitted. When the angle is determined, the implant connecting portion 3 is mounted on the concave portion Pa of the buried implant P to secure with a fixing screw 3g after inserting into the support hole 3d (refer to FIG. 4B).

Filling the bite material fixing portion 2 with the bite material 2b through a sheet material for height adjustment may make height adjustment easier, reduce the amount of the bite material 2b used, and prevent the misalignment. In order to make many records of occlusion, recording of occlusion may be made after varying the mounting angle against the implant P or after replacing with the jig 1A for bite alignment in dentistry with different lengths. Recording of occlusion may be made in the state in which the bite material fixing portion 2 in the eccentric position is directed towards the position of missed teeth (for example, position of missed back teeth). Since back teeth are frequently used as the reference for evaluating occlusion, such recording is effective to consistently construct artificial teeth. Furthermore, since bite registration is performed based on the implant P mounted on the alveolar bones in the present invention, a precise record for occlusion can be obtained.

Next, after the occlusal position of teeth is recorded with the bite material 2b arranged in the bite material fixing portion 2, the jig 1A for bite alignment in dentistry for recording the bite alignment (bite registration) is taken out to mount on the working model M for reproducing the state (FIG. 1, mounting on the articulator K in the figure) similar to actual oral cavity, and then, on the working model M, inspection is made or the prosthesis is made and adjusted. That is, the jig 1A for bite alignment in dentistry is reproduced on the working model M without using the conventional wax rim (S8). Therefore, there is no need for examining patients (S9) (see FIG. 14) and a burden to patients is reduced.

In the present embodiment, after an articulator is worn (S10), a metal frame is made according to the information reproduced (S11). In FIG. 14, "making an upper structure" means the products such as artificial tooth ridge and artificial teeth arranged on the implant.

After examining a patient, a try-in (investigation of attachment, occlusion, and teeth alignment of the artificial teeth) is then performed for adjustment to make the artificial teeth of the metal frame close to the final form (S12). After the try-in of the metal frame, the upper structure is fabricated (S13). After the above-mentioned reproduction is achieved, dental technicians may align the artificial teeth using the wax rim and perform the try-in in oral cavity to make the artificial teeth close to the final state. And then, the making of the artificial teeth is completed after checking bulging or the like in the lip and cheek of patients when clenching the artificial teeth in their mouth (S14).

By the way, among various types of dentures, impression taking for a complete denture is a creative work of "making" a mold. In complete dentures, not only the positional relationship between the mandible and the maxilla is ambiguous, but also the position in which the teeth are aligned in space is unclear, whereby a creative work is required. The present inventors then presume that it is useful to find a reference for determining the alignment of the teeth and the occlusal position. In onsite medical services, dentures currently used are sometime served for the reference. Anatomical features of oral cavity, the firmness of skin around mouth, and the face length are sometimes used as the reference. However, these references are more subjective to the movement and feeling of patients than impression.

Considering such aspects, the present inventors presume that it is important to take many records on occlusion. For this purpose, recording of occlusion at the location where back teeth are missed, recording of occlusion while patients intentionally clench the teeth out of position, and continuous recording of such occlusion are effective. To meet such requests occlusion at several positions is preferably recorded while the angle is varied using the jig 1A for bite alignment in dentistry comprising the bite material fixing portion in the eccentric position in the present embodiment or asking patients to intentionally clench the maxillary and mandibular teeth out of position.

Also, in the position in which the implant P is arranged (six positions in examples of FIGS. 1 and 2), performing bite registration by mounting the jig 1A for bite alignment in dentistry at all positions regardless of whether the denture is complete dentures or not is useful not only for making complete dentures but also provides a record of occlusion, for example, in one tooth among whole teeth, thereby improving precision in making only one artificial tooth.

Next, application examples of the present embodiment will be described.

Figure 6A:
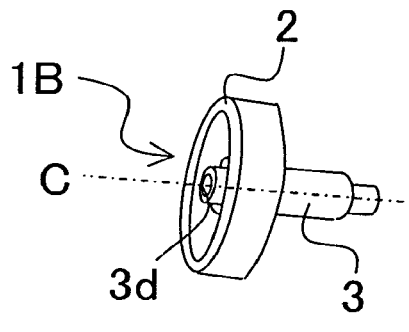
FIG. 6A is a perspective view of another jig for bite alignment in dentistry in the embodiment.
Figure 6B:
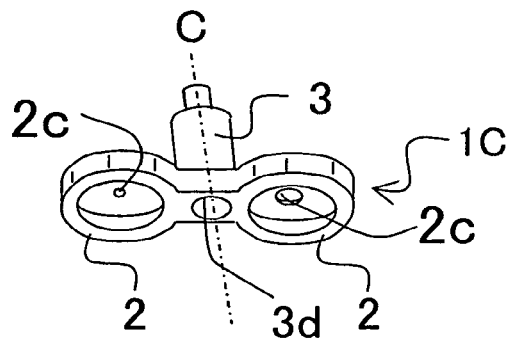
FIG. 6B is a perspective view of yet another jig for bite alignment in dentistry in the embodiment.
Figure 7A:
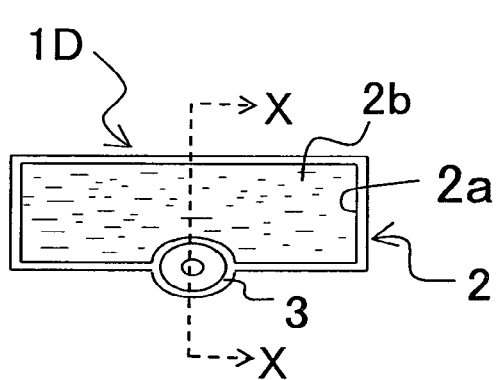
FIG. 7A is a plan view of yet another jig for bite alignment in dentistry of the embodiment.
Figure 7B:
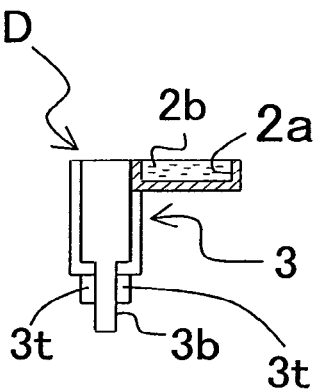
FIG. 7B is a section view of the jig taken along line X-X on FIG. 7A.

A jig for bite alignment in dentistry includes, as illustrated in FIG. 6A, the top-shaped jig 1B for bite alignment in dentistry in which the bite material fixing portion 2 is arranged on the central axis C of the implant connecting portion 3 and, as illustrated in FIG. 6B, the jig 1C for bite alignment in dentistry in which the bite material fixing portion 2 is bilaterally symmetric along the central axis C of the implant connecting portion 3. The top-shaped jig 1B for bite alignment in dentistry is used mainly for making one artificial tooth when one tooth is missed, but can be used for occlusion of plural teeth adjacent to each other by fabricating the bite material fixing portion 2 to be slightly oversized. That is, when one artificial tooth is constructed, the concave portion 2a of the bite material fixing portion 2 used is generally the same or smaller in size than the bite material fixing portion 2 itself, but the concave portion 2a of the bite material fixing portion 2 is slightly oversized for recording occlusion of plural teeth adjacent to each other. When one artificial tooth is constructed, the bite material fixing portion 2 is arranged at lower position than the height of adjacent tooth to fill the concave portion 2a having extra thickness with the bite material 2b.

Also, FIGS. 7A, 7B, 8A, and 8B illustrate the jigs 1D and 1E, respectively, for bite alignment in dentistry in which the bite material fixing portion 2 is rectangular. That is, occlusion of rectangular or arch-shaped but not circular teeth which are adjacent to each other and extended in the direction of the teeth arrangement can be recorded. The jig 1D for bite alignment in dentistry with the bilateral symmetry, the rectangular shape or the arch shape is suitable for constructing dentures with teeth adjacent to each other such as bridges.

Figure 8A:
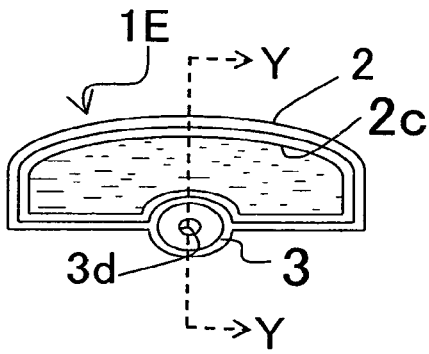
FIG. 8A is a plan view of yet another jig for bite alignment in dentistry of the embodiment.
Figure 8B:
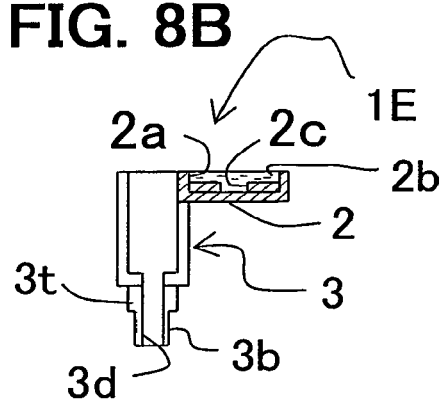
FIG. 8B is a section view of the jig taken along line Y-Y on FIG. 8A.

Also, as illustrated in FIGS. 8A and 8B, the bite material fixing portion 2 may be provided with the step 2c for enabling to prevent movement of the bite material 2b arranged in the lower side (alternative for the engaging hole 2c) or the position of the sheet-like member for intervention may be specified to prevent it from fall out.

Figure 9A:
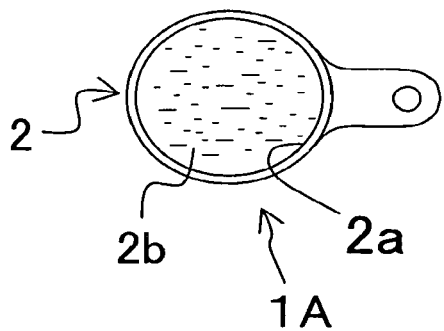
FIG. 9A is a plan view of the jig for bite alignment in dentistry of the embodiment.
Figure 9B:
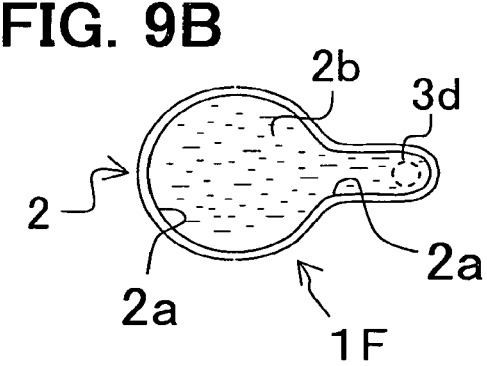
FIG. 9B is a plan view of yet another jig for bite alignment in dentistry of the embodiment.
Figure 10A:
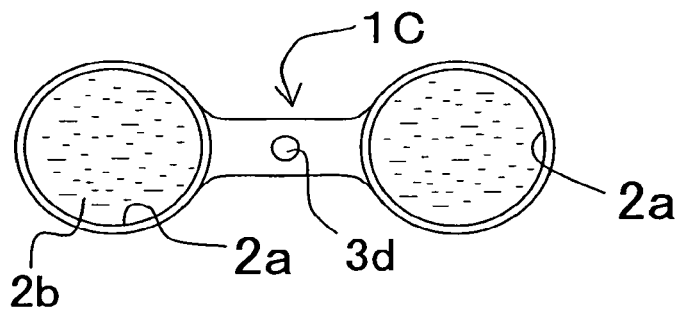
FIG. 10A is a plan view of the jig for bite alignment in dentistry of the embodiment.
Figure 10B:
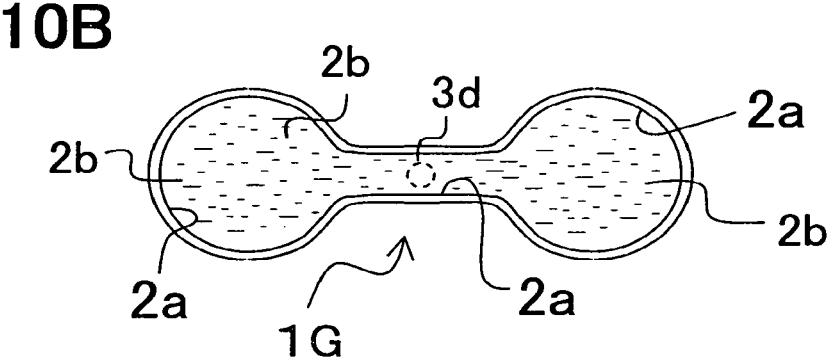
FIG. 10B is a plan view of yet another jig for bite alignment in dentistry of the embodiment.

Further, as illustrated in FIGS. 9B and 10B, the area of the concave portion 2a of the bite material fixing portion 2 in which the bite material 2b is arranged may be made larger. That is, FIGS. 9A and 10A illustrate the jigs 1A and 1C for bite alignment in dentistry described above, and as compared to these, in FIGS. 9B and 10B the disposition of the bite material 2b is extended to the support hole 3d of the implant connecting portion 3. The jigs 1E and 1G for bite alignment in dentistry are the jig with a larger area of the concave portion 2a of the bite material fixing portion 2 in which the bite material 2b is arranged. The support hole 3d can be fixed by secure connection without penetration depending on the types of fixing screw 3g.

Figure 12A:
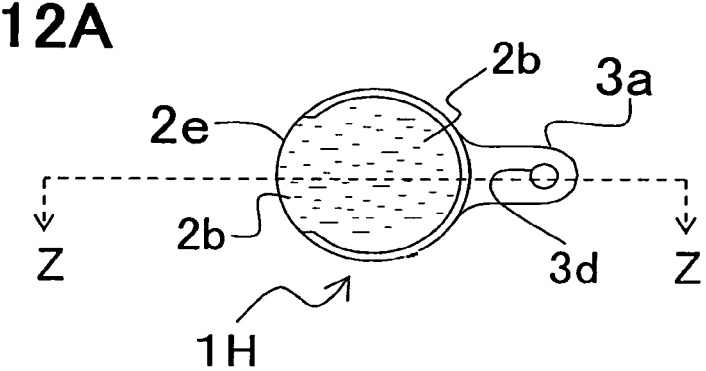
FIG. 12A shows a plan view of yet another jig for bite alignment in dentistry of the embodiment.
Figure 12B:
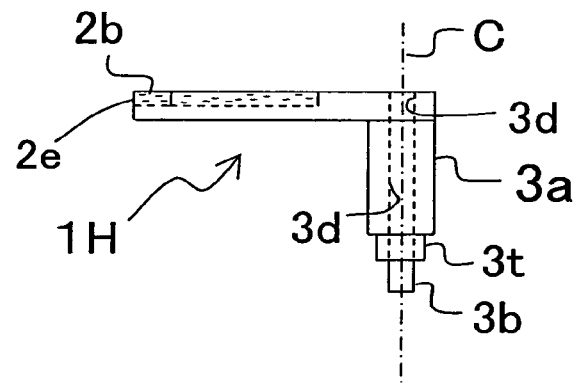
FIG. 12B shows a section view of the jig taken along line Z-Z on FIG. 12A.
Figure 13:
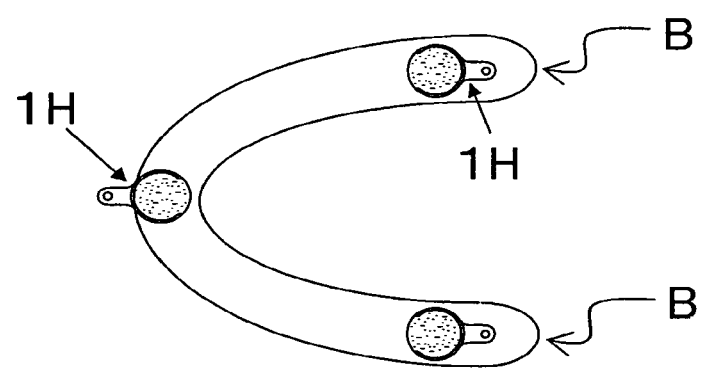
FIG. 13 shows an example for bite registration at plural positions in the embodiment.

Also, as illustrated in FIGS. 12A and 12B, the jig 1H for bite alignment in dentistry may be formed such that the tip of the concave portion 2b is notched for filling with the bite material 2b up to the tip 2e of the bite material fixing portion 2. As illustrated in FIG. 13, the jig 1H for bite alignment in dentistry is used for determining the occlusal position with plural (three) jigs 1H for bite alignment in dentistry using the U-shaped bite material B, and formed such that such a shape of the bite material B is readily arranged in the concave portion 2a of the fixing portion 2 of the jig 1H for bite alignment in dentistry. When bite registration is performed at plural positions as illustrated in FIG. 13, the outer circumferential surface of the implant connecting portion 3 and the concave portion Pa of the implant P without rotational restriction may be used.

As above, in the embodiment of the present invention, an example of complete dentures, a case of one artificial tooth, and a case of several artificial teeth adjacent to each other are described, but the jig for bite alignment in dentistry can be used for constructing any type of artificial teeth and of course, for reproducing and examining the state of oral cavity, and for explaining the findings to patients. Also, while complete dentures in the present embodiment are described in an example using a base called a metal frame, and a wax rim portion (gingival portion) can be manufactured based on the metal frame dentures, and all of them can be used in manufacturing complete dentures. These dentures can be also manufactured using a conventional wax rim. While in the present embodiment, an example in which the jigs 1A for bite alignment in dentistry is mounted at plural positions to determine the occlusal position is described, the jigs may be replaced at several positions to repeat the measurements several times for recording further detail of occlusion. Increase of the measurement frequency can reproduce the state of oral cavity with extremely high precision even when only one data is obtained by each measurement with a small jig for bite alignment in dentistry, thereby helping construction of dentures and investigation of the record on occlusion.

1A to 1H Jig for bite alignment in dentistry
2 Bite material fixing portion
2a Concave portion
2b Bite material
2c Engaging hole
3 Implant connecting portion
3c Step portion
3d Support hole
3g Fixing hole
3t Protrusion
B Bite material (U-shaped bite material)
C Central axis
K Articulator
P Implant
Pa Concave portion of implant
T Wax rim
M Working model (maxillary model)

The invention claimed is:

1. A jig for bite alignment in dentistry, comprising: one implant adapted to be arranged in an oral cavity;
a bite material fixing portion comprising a recess in which a bite material for recording an occlusal position of a tooth at a predetermined position adjacent to the one implant is contained; and
an implant connecting portion which is connected to the bite material fixing portion, and configured to attach to and detach from the one implant,
the bite material fixing portion is arranged offset from a central axis of the implant connection portion, and the implant connecting portion is attached to the one implant and the occlusal position of the tooth is recorded through the bite material contained in the bite fixing portion.

2. The jig for bite alignment in dentistry according to claim 1, wherein a cross-section of the implant connecting portion is formed in a shape of polygon so that a mounting angle of the implant connecting portion to the one implant is adjustable.

3. The jig for bite alignment in dentistry according to claim 2, wherein the recess has a circular shape extending from an end of the implant connecting portion at a right angle.

4. The jig for bite alignment in dentistry according to claim 3, wherein the recess has a predetermined depth that the bite material is filled therein.

5. A jig for bite alignment in dentistry for one implant arranged in an oral cavity, comprising:
a bite material fixing portion comprising a recess in which a bite material for recording an occlusal position of a tooth at a predetermined position adjacent to the one implant is contained and in which the tooth of which the occlusal position is recorded is inserted; and
an implant connecting portion which is connected to the bite material fixing portion, and configured to attach to and detach from the one implant,
wherein
the bite material fixing portion is arranged offset from a central axis of the implant connecting portion, and
the implant connecting portion is attached to the one implant and the occlusal position of the tooth is recorded through the bite material contained in the bite material fixing portion.

6. The jig for bite alignment in dentistry for one implant arranged in an oral cavity according to claim 5, further comprising a screw connecting the implant connecting portion and the one implant,
wherein a cross-section of the implant connecting portion is formed in a shape of polygon so that a mounting angle of the implant connecting portion to the one implant is adjustable.

7. The jig for bite alignment in dentistry for one implant arranged in an oral cavity according to claim 6, wherein the recess has a circular shape extending from an end of the implant connecting portion at a right angle.

8. The jig for bite alignment in dentistry for one implant arranged in an oral cavity according to claim 7, wherein the recess has a predetermined depth that the bite material is filled therein.

* * * * *